United States Patent [19]

Carson

[11] 4,048,191

[45] Sept. 13, 1977

[54] HALO-SUBSTITUTED 1-LOWERALKYL-5-AROYLPYRROLE-2-ACETIC ACID COMPOUNDS

[75] Inventor: John Robert Carson, Norristown, Pa.

[73] Assignee: McNeil Laboratories, Incorporated, Fort Washington, Pa.

[21] Appl. No.: 591,217

[22] Filed: June 27, 1975

[51] Int. Cl.² .......................................... C07D 207/34
[52] U.S. Cl. .............................. 260/326.47; 260/326.2; 260/326.46; 260/326.5 S; 260/326.5 J; 260/326.8 S; 260/326.9; 424/274
[58] Field of Search .................... 260/326.47, 326.5 J, 260/326.5 S

[56] References Cited

U.S. PATENT DOCUMENTS

| | | | |
|---|---|---|---|
| 3,655,693 | 4/1972 | Shen | 260/326.47 |
| 3,707,478 | 12/1972 | Carson | 260/326.47 |
| 3,721,680 | 3/1973 | Carson | 260/326.47 |
| 3,752,826 | 8/1973 | Carson | 260/326.5 J |
| 3,803,169 | 4/1974 | Carson | 260/326.5 J |
| 3,803,171 | 4/1974 | Carson | 260/326.47 |
| 3,835,149 | 9/1974 | Renfroe | 260/326.5 J |
| 3,846,447 | 11/1974 | Carson | 260/326.5 J |
| 3,952,012 | 4/1976 | Carson | 260/326.47 |
| 3,998,844 | 12/1976 | Carson | 260/326.47 |

Primary Examiner—Donald G. Daus
Assistant Examiner—Mary C. Vaughn
Attorney, Agent, or Firm—Geoffrey G. Dellenbaugh

[57] ABSTRACT

Halo-substituted 1-loweralkyl-5-aroylpyrrole-2-acetic acid compounds, useful for their anti-inflammatory activity.

12 Claims, No Drawings

HALO-SUBSTITUTED 1-LOWERALKYL-5-AROYLPYRROLE-2-ACETIC ACID COMPOUNDS

DESCRIPTION OF THE INVENTION

This invention relates to novel halo-substituted 1-loweralkyl-5-aroylpyrrole-2-acetic acid compounds, and particularly to compounds having the following formulas:

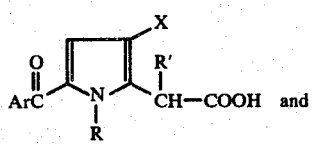

(Ia)

and

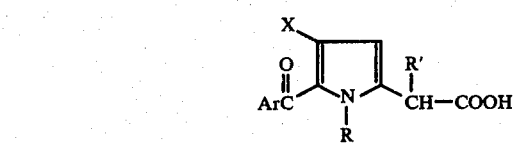

(Ib)

wherein X is a member selected from the group consisting of chloro and bromo, R is loweralkyl, R' is a member selected from the group consisting of hydrogen and loweralkyl (preferably methyl), and Ar is a member selected from the group consisting of phenyl and phenyl substituted with from one to three members each selected from the group consisting of halo, loweralkyl, and loweralkoxy (preferably methoxy), trifluoromethyl, methylthio, and methylsulfinyl; provided that no more than two are selected from the group consisting of trifluoromethyl, methylthio, and methylsulfinyl. A phenyl with a single substituent in the para position is the preferred substituted phenyl. "Loweralkyl" and "loweralkoxy" means a straight or branch chained, saturated, aliphatic hydrocarbon containing from one to about five carbon atoms such as, for example, methyl, ethyl, propyl, isopropyl, butyl, pentyl, and the like alkyls and, correspondingly, methoxy, ethoxy, propoxy, isopropoxy, pentoxy, and the like alkoxys. "Halo" includes fluoro, chloro, bromo, and iodo.

3-Halopyrroles

The compounds of formula (Ia) wherein Ar is other than methylsulfinylphenyl may be prepared by reacting an appropriate 1-loweralkyl-5-aroylpyrrole-2-acetic acid of formula (II) with a reagent capable of donating active bromine or chlorine, where X, R, R' and Ar are as previously defined. Stoichiometric amounts or an excess of such halogen donor is preferred. The reagent may be, for example, chlorine, sulfuryl chloride, N-chlorosuccinimide, or the like when X is chloro, or may be bromine, sulfuryl bromide, or the like when X is bromo. The preferred reagent is elemental chlorine or bromine. This reaction is conducted in a suitable solvent for halogenation such as, for example, a loweralkyl carboxylic acid (e.g., formic acid, acetic acid, propanoic acid, and the like), an inert halogenated hydrocarbon (e.g., chloroform, carbon tetrachloride, dichloromethane, and the like), or the like. Ambient temperature is preferred, but elevated temperatures may be employed to increase the rate of reaction. The product is isolated and purified by techniques well-known in the chemical art. This reaction may be illustrated by the following:

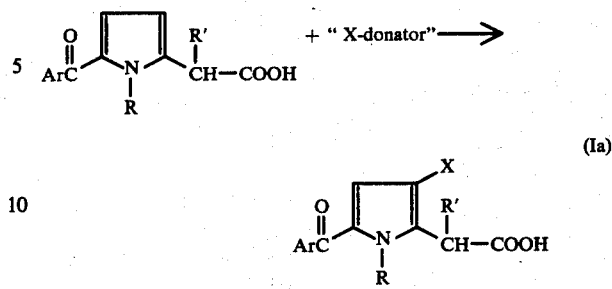

The compounds of formula (Ia) wherein Ar is other than methylsulfinylphenyl may also be prepared by reacting an appropriate loweralkyl 1-loweralkyl-5-aroylpyrrole-2-acetate of formula (III) with a reagent donating the appropriate active halogen (as described above), where X, R, R' and Ar are as previously defined and R'' is loweralkyl. Again, stoichiometric amounts or an excess of halogen donor is preferred. The resulting halogenated ester of formula (IV) is then hydrolyzed to yield the desired acetic acid derivative of formula (Ia). The halogenation reaction is conducted in a suitable solvent for halogenation as defined above, preferably at ambient temperature, but elevated temperatures may be employed to increase the rate of reaction. The resulting product may be purified by chromatographic techniques known in the chemical art to yield the pure halogenated ester (IV). Conventional ester-to-acid hydrolysis of this ester with acid or base catalyst, for example, by heating a solution of (IV) in aqueous ethanol with an alkali metal hydroxide to form the alkali metal salt of the acid and then acidifying the mixture, yields the acetic acid compound of formula (Ia). The foregoing reactions may be illustrated by the following:

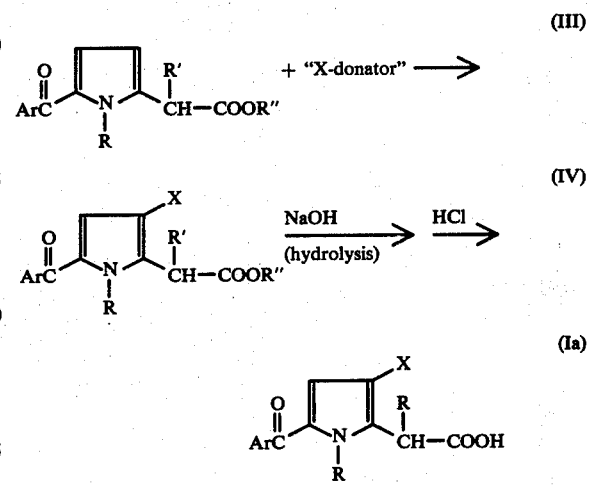

The compounds of formula (Ia) wherein Ar is methylsulfinylphenyl may be prepared by oxidation of the corresponding compounds of formula (Ia) wherein Ar is methylthiophenyl and X, R, and R' are as previously defined with an oxidizing agent such as hydrogen peroxide, sodium periodate, concentrated nitric acid, and the like. A slight excess of the oxidizing agent is presently employed, as are ambient temperatures. Lower alkanoic acids, such as glacial acetic acid, and aliphatic ketones such as acetone, are exemplary of the solvents in which this reaction may be conducted. The products may be isolated and purified by commonly-used laboratory procedures. This reaction is illustrated by the following:

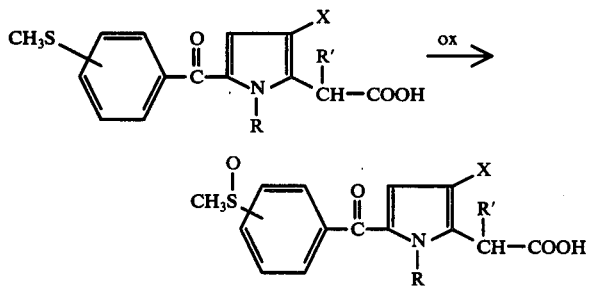

4-Halopyrroles: Preferred Method

The compounds of formula (Ib) wherein Ar is other than methylsulfinylphenyl may be prepared from the pyrrolidinium compounds of formula (X), which compounds may be obtained by the method of P.E. Sonnet, J. Org. Chemistry, 37, 925 (1972). By reduction of the pyrrolidinium compounds of formula (X), where X is as previously defined and Y is a suitable anion such as, for example, halide, perchlorate or the like, using hydrogen under elevated pressure and a suitable catalyst such as, for example, finely divided platinum oxide, rhodium on carbon, or the like, the corresponding pyrroles of formula (IX) may be obtained. A loweralkanol or a loweralkyl ester of a loweralkanoic acid is a suitable solvent. The temperature is preferably ambient and the initial hydrogen pressure is preferably about 50 p.s.i., although elevated temperatures and higher hydrogen pressures could be employed to increase the rate of reaction.

Alternatively, the compounds of formula (IX) may be prepared from those of formula (X), where X and Y are as previously defined, by a two-step reduction. The first step is the reduction of the pyrrolidinium compound of formula (X) by a boron hydride reducing agent such as diborane, lithium borohydride, and the like, with concomitant formation of a 1:1 complex between the reduction product and the reducing agent. This first step is conducted in a suitable inert organic solvent such as, for example, an ether (e.g. tetrahydrofuran, diethyl ether, etc), glyme, diglyme, and the like, and preferably at ambient temperature. Treatment of this complex with a base, for example pyrrolidine, in the second step causes removal of the borane from the complex to yield the desired compound (IX), which compound is purified by conventional extraction and recrystallization techniques. This second step is conducted in a suitable organic solvent or in the base itself (e.g., pyrrolidine) and preferably at ambient temperature.

Pyrroleacetonitriles of formula (VIII) may then be prepared by alkyl quarternization followed by cyanide displacement of the pyrrolidine ring of compounds (IX). Typical quaternizing agents are diloweralkyl sulfate, loweralkyl iodide, methyl tosylate, or the like. A suitable dipolar, aprotic solvent should be used such as, for example, dimethyl sulfoxide, dimethylformamide, hexamethylphosphorus triamide and the like. Stoichiometric amounts are preferred, as is cooling during the reaction. The quarternary salt is then treated in situ with a slight molar excess of an alkali metal cyanide such as, for example, sodium cyanide, potassium cyanide, or the like. Ambient temperature is preferred, but elevated temperatures may be employed to increase the rate of reaction. The resulting acetonitrile is purified by conventional extraction techniques. It should be understood that the above reaction would be equally successful if compound (IX) were a 2-dialkylaminomethyl-4-halopyrrole.

From the 5-unsubstituted compounds of formula (VIII) the corresponding substituted pyrroles of formula (VII) may be prepared by conventional Friedel-Crafts acylation using an appropriate aroyl chloride, where X and Ar are as previously described, and a Lewis acid such as, for example, aluminum chloride, stannic chloride, or the like. Stoichiometric amounts are preferably employed. A halogenated hydrocarbon such as, for example, dichloromethane, 1,2-dichloroethane, or the like; nitrobenzene; carbon disulfide; and the like are suitable solvents. The product may be isolated by conventional extraction techniques. The foregoing reaction schemes may be illustrated by the following:

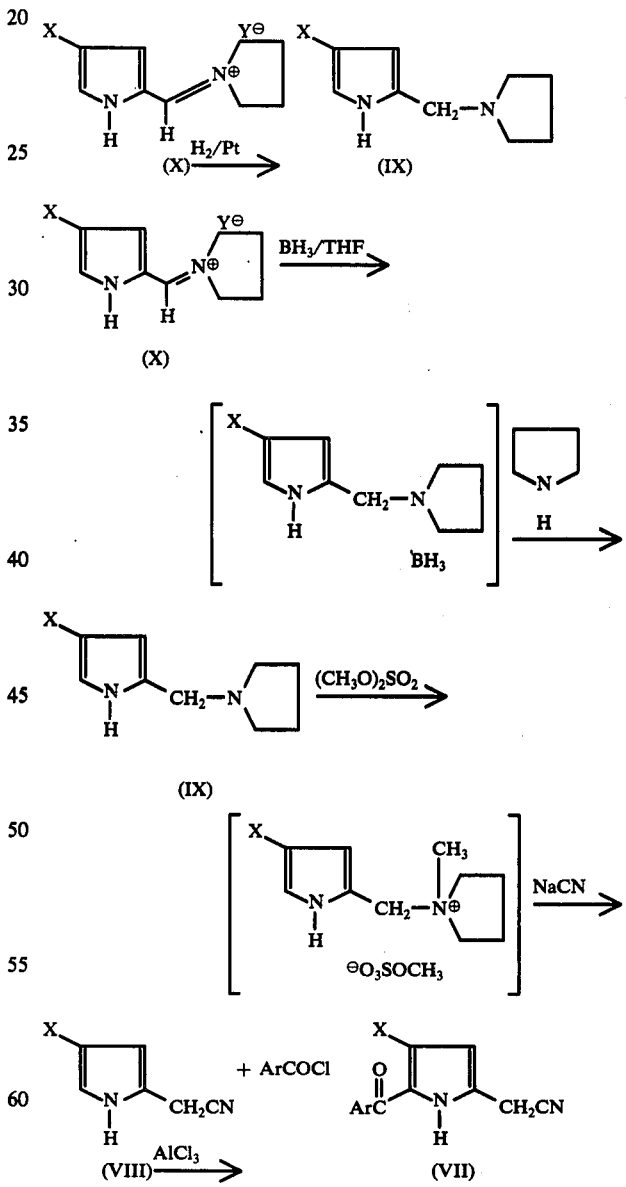

N-alkylation of the 1-unsubstituted pyrrole of formula (VII) yields the corresponding N-alkylpyrrole of formula (VI). Typical alkylating agents include di-loweralkyl sulfate, loweralkyl iodide, or the like, where R is as previously defined, preferably used in slight molar excess. The reaction is conducted in an inert aprotic solvent such as, for example, an aromatic hydrocarbon (e.g., benzene, toluene, and the like), an ether (e.g., tetrahydrofuran, diethyl ether, glyme, diglyme, and the like), a secondary or tertiary loweralkanol (e.g., isopropanol, tertbutanol, and the like) dimethylformamide, dimethylsulfoxide, and the like in the presence of a slight molar excess of a strong base such as for example, an alkali metal amide, hydride, or alkoxide; e.g., sodium amide, sodium hydride, sodium isopropoxide, sodium tert-butoxide, and the like. The product may be purified by chromatographic techniques known in the art.

From these N-alkylpyrroles may be obtained α-alkylpyrrole of formula (V) by conventional C-alkylating techniques; e.g., with a loweralkyl halide as the alkylating agent in the presence of a strong base such as sodium amide or sodium hydride. Then by conventional nitrile-to-acid hydrolysis of the 2-acetonitile derivative of formula (V) or formula (VI) with either acid or base catalyst, for example, by heating with aqueous or alcoholic alkali or by refluxing with aqueous sulfuric acid (20–70%) or with concentrated hydrochloric or hydrobromic acid, the product of formula (Ib) is obtained. If base catalysis is used, the resultant alkali metal salt of the acid is converted to the acid form. This reaction scheme may be illustrated by the following:

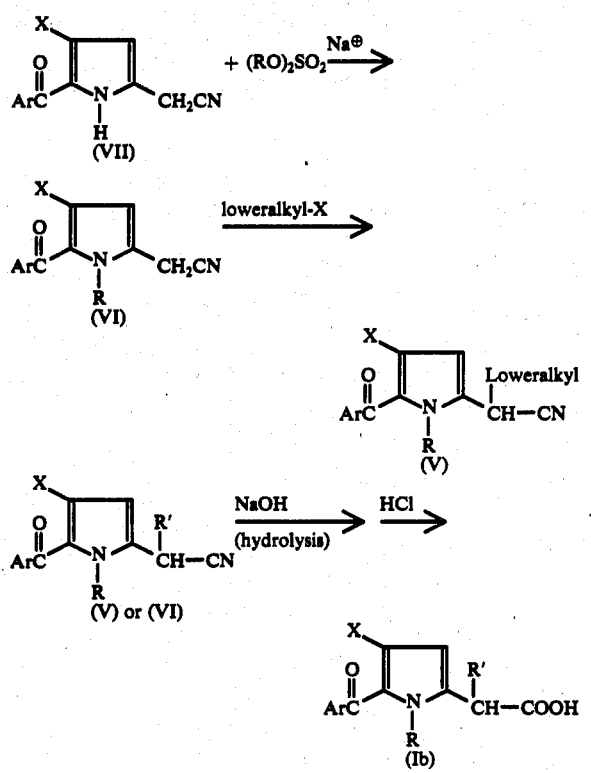

4-Bromopyrroles: Less Preferred Methods

The compounds of formula (Ib) wherein Ar is other than methylsulfinylphenyl and where X is bromo may be obtained from the dicarboxypyrroles of formula (XIV) where Ar and R are as previously defined by the following procedure. The acetic acid group on the dicarboxypyrrole is esterfied by partial esterification procedures known in the art. For example, the reaction is conducted in an appropriate loweralkanol of formula HOR", where R" is loweralkyl, in the presence of a catalytic amount of a strong acid such as hydrogen chloride gas and preferably at reflux temperature. Esterification of the 3-carboxyl group can easily be avoided by use of mild esterification conditions because such esterification occurs much less readily than that of the 2-acetic acid group.

The decarboxylation of the compounds of formula (XIII) yields the 2-unsubstituted pyrrole of formula (XII). Decarboxylation may be produced by heating compound (XIII) at about 200°–250°C in the absence of oxygen (preferably under nitrogen). A catalytic amount of, for example, copper chromite in a suitable solvent such as, for example, quinoline, may be added to increase the rate of reaction. The product may be isolated and purified by conventional extraction and recrystallization techniques.

The α-alkyl compounds of formula (XI) may be prepared by conventional C-alkylation of the α-unsubstituted compounds of formula (XII) according to conventional procedures known in the art.

Conventional ester-to-acid hydrolysis of the ester of formula (XI) or formula (XII) yields the desired pyrrole-2-acetic acid or formula (Ib). This reaction scheme may be illustrated by the following:

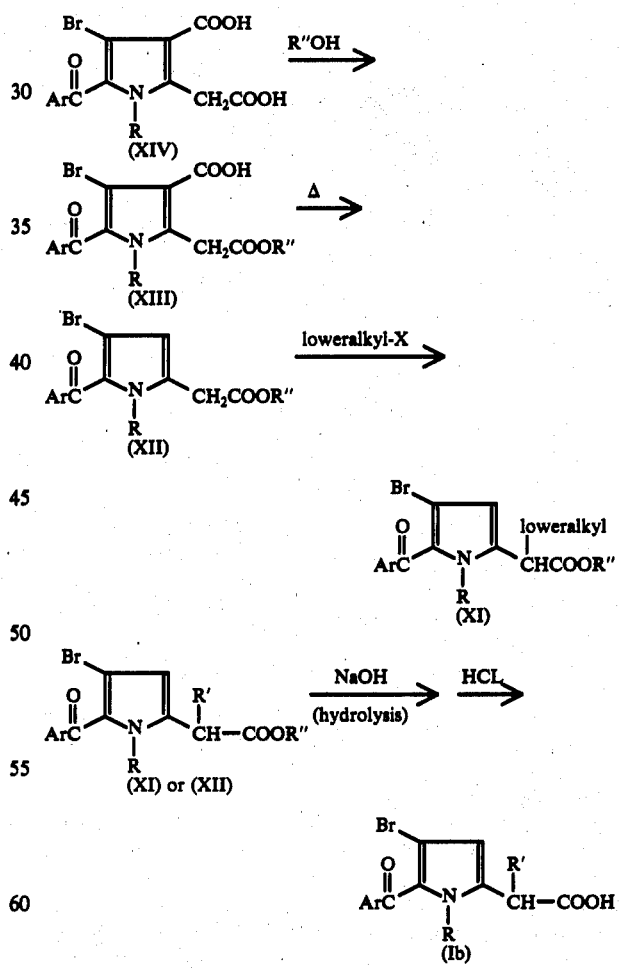

The compounds of formula (XIV) may be prepared by two alternate schemes. The first scheme begins with condensation of a diloweralkyl acetonedicarboxylate, a loweralkylamine, and chloroacetaldehyde, all as generally known in the art.

The first ingredient is rapidly added to a solution of the second, preferably an aqueous solution cooled in ice. The third ingredient is then added slowly with cooling to keep the temperature of the reactants below about 40,20 C, after which the whole is stirred at ambient temperature. The resultant product of formula (XVII) is isolated and purified by conventional extraction and recrystallization techniques.

Then by standard Friedel-Crafts acylation of a compound of formula (XVII), the 2-acyl-dicarboxypyrrole of formula (XVI) is prepared.

Then the 4-bromo compounds of formula (XV) may be obtained by reacting the 4-unsubstituted compound of formula (XVI), where R,Ar, and R'' are as previously defined and R''' is loweralkyl, with a reagent delivering active bromide, as previously defined, in a suitable halogenation solvent as previously defined. Ambient temperature is preferred, but elevated temperatures may be employed to increase the rate of reaction.

Finally, the compounds (XIV) may be prepared by conventional hydrolysis of di-esters of formula (XV), where R, Ar, R'', and R''' are as previously defined by standard techniques. This reaction scheme may be illustrated by the following:

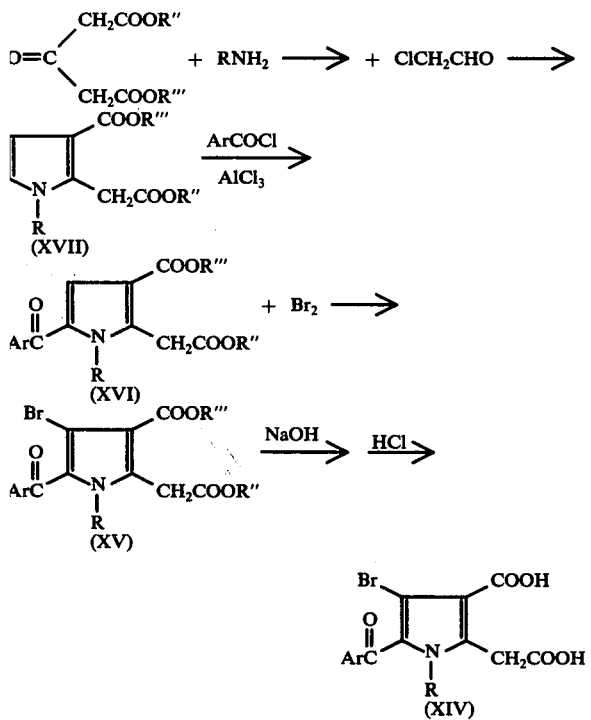

The second scheme begins with conventional Freidel-Crafts acylation of a compound of formula (XXII) with ArCOCl, where R, Ar, and R''' are as previously defined to yield the compounds of formula (XXI). The compounds of formula (XXII) are generally known and may be prepared by the method of H. Sashara, S. Misaki, and E. Inomoto, Nippon Kakagu Zasschi, 83, 637 (1962).

Then by brominating the 4-unsubstituted compounds of formula (XXI), where R, Ar, and R'' are as previously defined, 4-bromo compounds of formula (XX) may be prepared. A bromine donator, as previously defined, is employed, preferably elemental bromine. The reaction is conducted in a suitable halogenation solvent, as previously defined, and preferably at reflux temperature. A catalytic amount of iodine crystals is also preferably employed. The product may be isolated and purified by conventional extraction techniques.

The next step is to brominate the 2-methyl group by reaction with a free radical brominating agent such as, for example, N-bromosuccinimide in suitable inert solvent such as, for example, an aromatic hydrocarbon (e.g., benzene, and the like), a halogenated aliphatic hydrocarbon (e.g., chloroform, carbon tetrachloride, dichloromethane, and the like), or the like. Stoichiometric amounts or an excess of brominating agent is preferred. A catalytic amount of a free radical initiator such as dibenzoyl peroxide is also employed to initiate the reduction. The reaction is preferably conducted at reflux.

Then by cyanation of the 2-bromomethyl compounds of formula (XIX), the 2-acetonitrile compounds of formula (XVIII) are prepared. The reaction is conducted in a dipolar, aprotic solvent such as, for example, dimethyl sulfoxide, by addition of a solution of compound (XIX) to a suspension of an alkali metal cyanide, preferably at such a rate that the temperature of this reaction remains about 45° C. Stoichiometric amounts are preferred. After addition is complete, the mixture is stirred, and the product is isolated and purified by conventional extraction, chromatographic and recrystallization techniques.

Finally, the desired compound (XIV) may be obtained by conventional nitrile-to-acid hydrolysis of the acetonitrile of formula (XVIII) by methods previously discussed. The reaction scheme may be illustrated by the following:

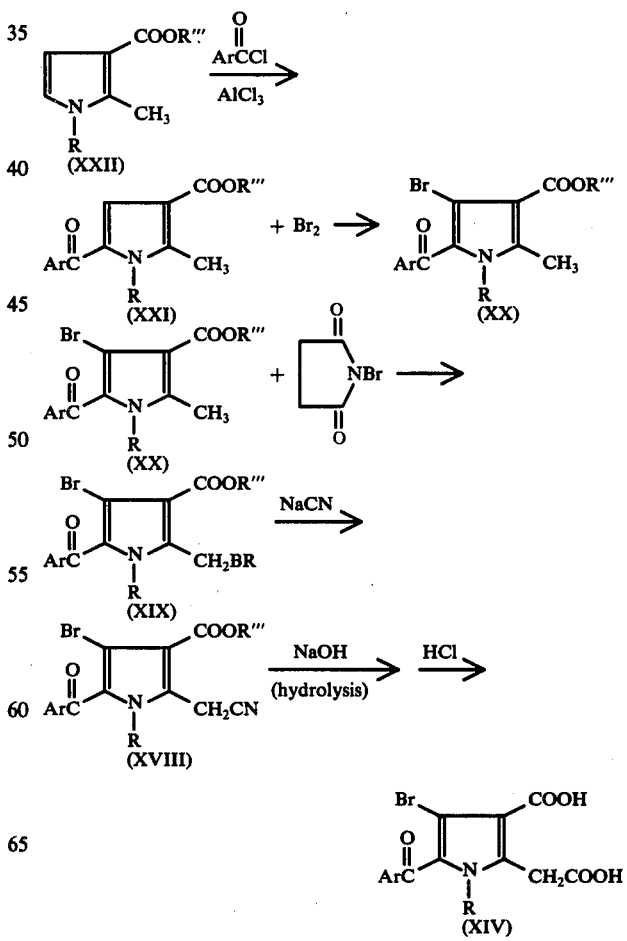

The compounds of formula (Ib) wherein Ar is methylsulfinylphenyl may be prepared by oxidation of the corresponding methylthiophenyl-2-acetonitrile compound of formulas (V) or (VI), wherein X, R, and R' are as previously defined, with an oxidizing agent such as hydrogen peroxide, sodium periodate, concentrated nitric acid, and the like. A slight excess of the oxidizing agent is preferred, as are ambient temperatures. Lower alkanoic acids such as glacial acetic acid and aliphatic ketones such as acetone are exemplary of the solvents in which this reaction may be conducted. The resulting methylsulfinylphenyl- 2-acetonitrile compound of formula (XXIII) may be isolated and purified by commonly-used laboratory procedures, after which it may be hydrolyzed to the desired methylsulfinylphenyl- 2-acetic acid compound by conventional nitrile-to-acid hydrolysis as for compounds (V) and (VI). This reaction scheme may be illustrated by the following:

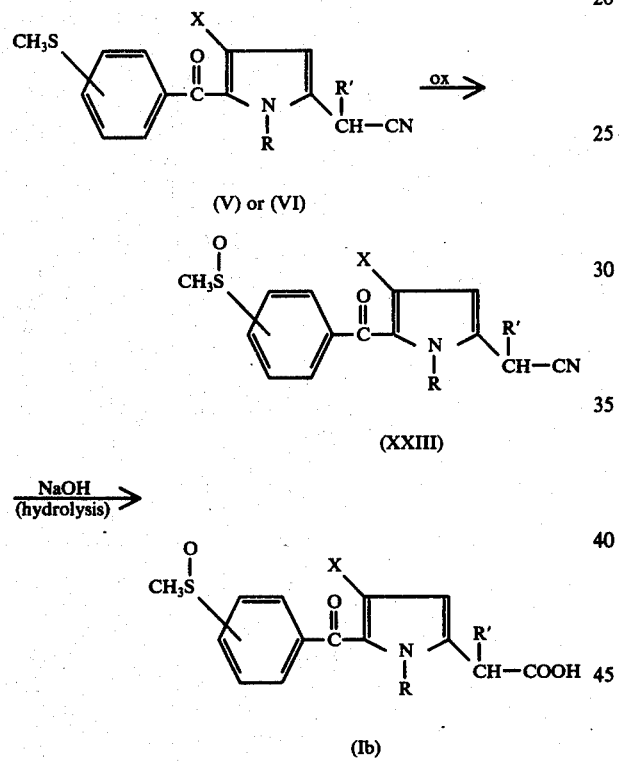

The compounds of formula (Ia) and (Ib) possess antinflammatory activity as evidenced by activity in at least one of the following three tests at dosages of from about 1 mg/kg to about 200 mg/kg body weight.

Test A: Kaolin-Induced Rat-Paw Edema Assay

In the kaolin-induced rat paw edema assay, the ability of a compound, when administered in a single oral dose, to inhibit the swelling of the rat paw injected with a standard amount (0.1 ml.) of 10% kaolin suspension in saline is measured. For comparative purposes, the activity of the compound to be tested is measured against that produced by the known anti-inflammatory agent, phenylbutazone. Male Holtzman rats are used in the assay. For example, in this test, the compound 3-chloro-1-methyl-5-(p-toluoyl)pyrrole-2-acetic acid exhibits an inhibition of 32% at 12.5 mg/kg and 47% at 25 mg/kg. Phenylbutazone, for comparison, exhibits an inhibition of 30–40% at 80 mg/kg and 50–60% at 100 mg/kg.

Test B: Carrageenan-Induced Edema Test

Test A above is repeated using a 1.0% saline solution of carrageenan in place of the 10% saline solution of kaolin used therein. In this test, the compound 3-bromo-1-methyl-5-(p-toluoyl)-2-acetic acid exhibits inhibition of 42% at 200 mg/kg and the compound 4-bromo-1-methyl-5-(p-toluoyl)pyrrole-2-acetic acid exhibits an inhibition of 23% at 9 mg/kg.

Test C: Adjuvant Arthritis Test

This test is reported in Wong, et al., J. Pharm, and Exp. Ther. 185:127 (1973). In this test, the compound 4-chloro-5-(p-chlorobenzoyl)-1-methyl- pyrrole-2-acetic acid exhibits 58.6% inhibition at 2.5 mg/kg and the compound 4-bromo-5-(p-chlorobenzoyl)-1-methyl-pyrrole- 2-acetic acid exhibits 61.8% inhibition at 2 mg/kg.

The novel 1-unsubstituted compounds of formula (VII) and the novel acetate ester compounds of formulas (IV) and (XI) wherein X, R, R', and Ar are as previously defined and wherein R" is loweralkyl, are also considered to be within the scope of the present invention. They are useful as intermediates in the preparation of the pharmacologically useful compounds of formulas (Ia) and (Ib); in addition, the esters of formula (XI) are also useful for their anti-inflammatory activity. These intermediates may be illustrated by the following:

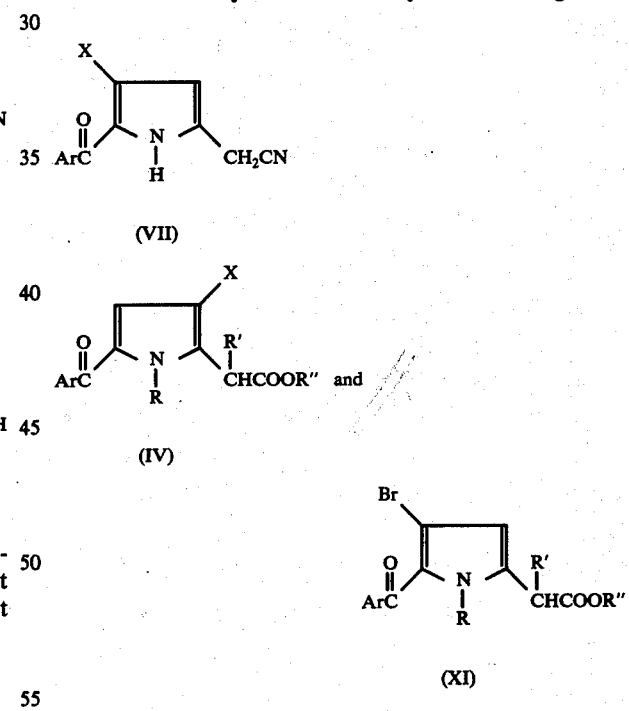

The following examples are intended to illustrate, but not to limit, the scope of the present invention.

EXAMPLE I

3-Bromo-1-methyl-5-(p-toluoyl)pyrrole-2-acetic acid

To a stirred solution of 2.0g. (0.0078 moles) of 1-methyl- 5-(p-toluoyl)pyrrole-2-acetic acid in 40 ml. of glacial acetic acid is added dropwise a solution of 1.2g (0.0078 moles) of bromine in 3 ml. of glacial acetic acid. The mixture is stirred at room temperature for two hours, after which it is poured into 300 ml. of water, and the solid which forms is filtered off. Recrystallization from ether-hexane yields 3-bromo-1-methyl-5-(p-toluoyl) pyrrole-2-acetic acid as a white solid; m.p. 162°–164° C.

Analysis: Calc'd. for $C_{15}H_{14}O_3BrN$: C, 53.59; H, 4.19% Found: C, 53.56; H, 4.11%.

EXAMPLE II

Methyl 3-chloro-1-methyl-5-(p-toluoyl)pyrrole-2-acetate

A solution of 4.26g (0.06 mole) of chlorine in 75 ml. of chloroform is added rapidly to a mixture of 16.2g. (0.06 mole) of methyl 1-methyl-5-(p-toluoyl)- pyrrole-2-acetate, 16g (0.12 mole) of calcium carbonate, and 0.48g. (0.003 mole) of ferric chloride in 75 ml. of chloroform. The temperature rose somewhat. After an hour, when the chlorine has been consumed, the solids are removed by filtration and the filtrate is evaporated in vacuo to yield a red oil. The oil is chromatographed on 2lb. of Silica (Mallinkrodt SILIC-AR CC-4) 100–200 mesh and eluted successively with hexane, benzene, and chloroform. The first compound-bearing fraction is eluted with chloroform. The solvent is evaporated and the residue is recrystallized from methanol to give white crystalline methyl 3-chloro-1-methyl-5-(p-toluoyl)pyrrole-2-acetate; m.p. 144°–146° C.

Analysis: Calc'd. for $C_{15}H_{14}C\,1NO_3$: C, 61.76; H, 4.83; N, 4.82%. Found: C, 61.83; H, 4.99; N (K), 4.86%.

EXAMPLE III

3-Chloro-1-methyl-5-(p-toluoyl)pyrrole-2-acetic acid

A suspension of 3.3 g. of methyl 3-chloro-1-methyl-5-(p- toluoyl)pyrrole-2-acetate (0.0108 mole) from Example II in 12 ml. of 1N sodium hydroxide and 5 ml. of ethanol is refluxed for 30 min. The ethanol is evaporated from the yellow solution, and the latter is poured into dilute HCl. The precipitate is collected, air dried, and recrystallized from 2-propanol to give 3-chloro-1-methyl-5-(p-toluoyl) pyrrole-2-acetic acid as a white solid; m.p. 163°–164° C (dec.)

EXAMPLE IV 1-(Pyrrol-2-ylmethylene)pyrrolidinium perchlorate

A suspension of 237.0 g. (1.38 mole) of pyrrolidine perchlorate in 500 ml. of benzene and 500 ml. of ethyl acetate is stirred and refluxed with water separation for 1 hr., then cooled to room temperature. 131.2 g. (1.38 mole) pyrrole-2-carboxaldehyde is added and the reaction mixture is stirred and refluxed with water separation for 6 hrs. After the whole has been cooled in an ice bath, the solvent is decanted from the solid product, and the product is recrystalllized from 1:1 acetonitrile/ether to give 1-(pyrrol- 2-ylmethylene)-pyrrolidinium perchlorate as a yellow solid; m.p. 100°–102° C.

EXAMPLE V 1-(4-Chloropyrrol-2-ylmethylene)pyrrolidinium perchlorate

To a stirred suspension of 215.4 g. (0.865 moles) of the product of Example IV in 4 liters of dichloroethane at 0° C. is added dropwise 116.8g. (0.865 moles) of freshly distilled sulfuryl chloride. After addition is complete (about 40 minutes), the reaction mixture is allowed to warm to ambient temperature and is stirred for about 4 hours, after which the solvent is evaporated to give a tan residue. Recrystallization of this residue from dichloroethane/ether gives 1-(4-chloropyrrol-2-ylmethylene) pyrrolidinium perchlorate; m.p. 122°–126° C.

EXAMPLE VI

4-Chloro-2-(1-pyrrolidine methyl)pyrrole perchlorate

A suspension of 114.4 g. (0.404 mole) of the product of Example V in 1 l of ethyl acetate is shaken with 1.2 g of platinum oxide under an initial hydrogen pressure of 48 psi. After being shaken for 72 hours, the reaction mixture is filtered and the filter cake is washed exhaustively with ethyl acetate. The filtrate is evaporated to give 4-chloro- 2-(1-pyrrolidinomethyl)pyrrole perchlorate as a brown oil.

EXAMPLE VII

4-Chloropyrrole-2-acetonitrile

An aqueous solution of 114.0 g. of the product of Example VI is converted into the free base form by addition of 10% aqueous sodium hydroxide solution. The solid that is thus precipitated is filtered, washed with water and dried to give 67.1 g. (0.364 mole) of free base. The free base is dissolved in 350 ml. of dry dimethyl sulfoxide and stirred in an ice bath while 45.9 g. (0.364 mole) of dimethyl sulfate is added dropwise. The whole is then stirred for a half hour and warmed to room temperature, whereupon 20.0 g. (0.41 mole) of freshly ground and dried sodium cyanide is added all at once. After the resulting solution has been stirred for 2 hours at ambient temperature, it is poured onto ice and this aqueous solution is extracted four times with 250 ml. of diethyl ether. The combined ether extracts are washed successively with brine, 3N hydrochloric acid solution, aqueous sodium bicarbonate solution, and brine, and are dried over sodium sulfate. Evaporation of the ether yields 4-chloropyrrole-2-acetonitrile as a brown oil.

EXAMPLE VIII

4-Chloro-5-(p-chlorobenzoyl)pyrrole-2-acetonitrile

The 4-chloropyrrole-2-acetonitrile produced in Example VII is dried by dissolving it in 3 liters of absolute ether and filtering the resulting solution through 400 g. of silica gel. The filter cake is washed well with ether, the washings are combined with the filtrate and the whole is evaporated to yield a dry sample of 4-chloropyrrole-2-acetonitrile. To a stirred solution of 42.1 g. of this dried material in 60 ml. of dichloroethane in an ice bath is added dropwise a solution of 40.0 g. (0.30 mole) of anhydrous aluminum chloride and 32.5 g. (0.30 mole) of p-chlorobenzoyl chloride in 120 ml. of dichloroethane over a period of 30 minutes. After this addition is complete, the whole is rapidly heated to reflux and is refluxed for about 3 minutes, after which it is poured into ice-water. The resulting organic and aqueous layers are separated and the latter is extracted three times with chloroform. The combined organic solutions are washed successively with aqueous dimethylamino-n- propylamine solution, 3N hydrochloric acid solution, aqueous sodium bicarbonate solution, and brine, and are dried over magnesium sulfate. Evaporation of the solvents yields a black semi-solid which is recrystallized twice from methanol in the presence of activated charcoal to give 4-chloro-5-(p-chlorobenzoyl) pyrrole-2-acetonitrile as a greyish solid; m.p. 194°–197° C.

EXAMPLE IX

4-Chloro-5-(p-chlorobenzoyl)-1-methylpyrrole-2-acetonitrile

To a refluxing solution of sodium isopropoxide in isopropanol (prepared by refluxing 0.69 g. (0.030 mole) of sodium in 70 ml. of isopropanol) is added 7.0 g. (0.025 mole) of 4-chloro-5-(p-chlorobenzoyl)-pyrrole- 2-acetonitrile prepared according to Example VIII, after which a solution of 3.78 g. (0.030 mole) of dimethyl sulfate in 10 ml. of isopropanol is added dropwise. When addition of the dimethyl sulfate solution is complete, the whole is refluxed for a half-hour and then poured into 1 liter of ice water. Filtration of the resulting mixture yields a grey solid, which is washed well with water and is then chromatographed with benzene on alumina. The chromatographed material is finally recrystallized from isopropanol to yield 4-chloro-5-(p-chlorobenzoyl)-1-methyl- pyrrole-2-acetonitrile as a beige solid; m.p. 139°-142° C.

EXAMPLE X

4-Chloro-5-(p-chlorobenzoyl)-α-methyl-1-methylpyrrole-2- acetonitrile

To a suspension of 12.2g. of 50% sodium hydride (mineral oil) in 1,2-dimethoxyethane is added 70 g. (0.24 mole) of 4-chloro-5-(p-chlorobenzoyl)-1-methylpyrrole-2- acetonitrile in 1,2-dimethoxyethane over a period of one half hour at room temperature. After the addition is complete, the whole is stirred for one hour and then 35 g. (0.25 mole) of methyl iodide is added. The reaction mixture is stirred for an additional 3 hours and is concentrated in vacuo; the residue is diluted with water and extracted with chloroform. After the extract is dried the chloroform is removed, leaving a brown solid residue which, upon trituration with cold water, yields 4-chloro-5- (p-chlorobenzoyl)-α-methyl-1-methylpyrrole-2-acetonitrile.

EXAMPLE XI

4-Chloro-5-(p-chlorobenzoyl)-1-methylpyrrole-2-acetic acid

A solution of 4.3 g. (0.015 mole) of 4-chloro-5- (p-chlorobenzoyl)-1-methylpyrrole-2-acetonitrile and 1.2 g. (0.030 mole) of sodium hydroxide in 11 ml. of deionized water and 20 ml. of 95% ethanol is stirred and refluxed for seven hours and is then stirred at ambient temperature for about 18 hours. The precipitate which results when this reaction mixture is poured into 500 ml. of dilute hydrochloric acid is filtered off, washed with water, and recrystallized once from acetonitrile and once from diethyl ether in a Soxhlet extractor to give 4-chloro-5-(p-chlorobenzoyl)-1- methylpyrrole-2-acetic acid as a buff solid; m.p. 203°-204° C. (dec.)

Analysis: Calc'd for $C_{14}H_{11}Cl_2NO_3$: C, 53.87; H, 3.55%. Found: C, 53.97; H, 3.57%.

EXAMPLE XII

Ethyl 3-Ethoxycarbonyl-1-methylpyrrole-2-acetate

To a cooled solution (5° C) of 380 g. of 40% aqueous methylamine is rapidly added 196 g. (0.96 mole) of diethyl acetonedicarboxylate, whereupon the temperature of the solution rises to about 25° C. To the resulting solution is then added 510 g. of 30% aqueous chloroacetaldehyde at a rate such that the temperature of the solution stays below 40° C with ice cooling. After this addition is completed, the whole is stirred for 1 hour at room temperature and is then poured into a mixture of ice and hydrochloric acid. This resulting mixture is extracted with diethyl ether, and the ether extract is washed with aqueous sodium bicarbonate solution and brine, and is dried over magnesium sulfate. Evaporation of the solvent in vacuo and recrystallization of the residue thereby obtained from isopropanol and then ether-hexane yields ethyl 3-ethoxy- carbonyl-1-methylpyrrole-2-acetate as a white solid; m.p. 58°-60° C.

EXAMPLE XIII

Ethyl 5-(p-chlorobenzoyl)-3-ethoxycarbonyl-1-methylpyrrole-2-acetate

A solution of 28 ml. (0.22 mole) of p-chlorobenzoyl chloride and 29.4 g. (0.22 mole) of aluminum chloride in 160 ml. of 1,2-dichloroethane (DCE) is added to a refluxing solution of 52.7 g. (0.22 mole) of ethyl 3-ethoxycarbonyl-1-methylpyrrole-2-acetate in 160 ml. of DCE. The mixture is heated under reflux for 4½ hours, after which it is poured into ice-hydrochloric acid. The mixture is extracted with $CHCl_3$ and the extract is washed successively with dimethyl-amino-n-propylamine solution, dilute hydrochloric acid, and brine, and is dried over magnesium sulfate. Evaporation of the solvent in vacuo and chromotographing the resulting residue on silica gel with a benzene to ether gradient yields the desired product in the first compound-bearing fractions. The solvent is evaporated from these combined fractions, and the resulting residue is recrystallized successively from methylcyclohexane and isopropanol to yield ethyl 5-(p-chlorobenzoyl)-3-ethoxy -carbonyl-1-methylpyrrole-2-acetate as a white solid; m.p. 91°-93° C.

EXAMPLE XIV

Ethyl 4-bromo-5-(p-chlorobenzoyl)-3-ethoxycarbonyl-1-methylpyrrole-2-acetate

A solution of 20 g. (0.053 mole) of ethyl 5-p-chlorobenzoyl-3-ethoxycarbonyl-1-methylpyrrole- 2-acetate in 200 ml of chloroform containing a few crystals of iodine as catalyst is heated to reflux and a solution of 3.0 ml (0.058 mole) of bromine in 20 ml of CH $Cl_3$ is added over 45 min. The whole is heated under reflux for 1½ hours, cooled, and washed successively with aqueous sodium bicarbonate solution, aqueous sodium bisulfite solution and brine. After the solution is dried over magnesium sulfate, the solvent is evaporated in vacuo and the resulting residue is recrystallized successively from methycyclohexane and 75% ethanol-water to give ethyl 4-bromo-5-(p-chlorobenzoyl)-3- ethoxycarbonyl-1-methylpyrrole-2-acetate as white crystals; m.p. 88°-90° C.

EXAMPLE XV

4-Bromo-3-carboxy-5-p-chlorobenzoyl-1-methyl-pyrrole-2-acetic acid

A 17.8 g. sample of ethyl 4-bromo- 5-p-chlorobenzoyl-3-ethoxycarbonyl-1-methylpyrrole-2acetate in 200 ml of 25% sodium hydroxide is stirred at 95° C. for 2 hours. It is then poured into ice-hydrochloric acid and the resulting solid 4-bromo-3-carboxy-5-p-chlorobenzoyl-1- methylpyrrole-2-acetic acid is collected and dried; m.p. 261° -263° C.

EXAMPLE XVI

Ethyl 4-Bromo-3-carboxy-5-p-chlorobenzoyl-1-methylpyrrole-2-acetate

A suspension of 16.8 g. of 4-bromo-3-carboxy-5-p-chlorobenzyl-1-methylpyrrole-2-acetic acid in 170 ml of 0.5% ethanolic hydrogen chloride is heated under reflux for 45 min. The solution is filtered and cooled and the resulting precipitated solid is collected. A second crop is then obtained by partial evaporation of the filtrate. The combined crystalline material is recrystallized from benzene to give ethyl 4-bromo-3-carboxy-5-p-chlorobenzoyl-1- methylpyrrole-2-acetate; m.p. 183°-185° C.

EXAMPLE XVII

Ethyl 4-Bromo-5-(p-chlorobenzoyl)-1-methylpyrrole-2-acetate

A 7.2 g. sample of ethyl 4-bromo-3-carboxy-5-p- chlorobenzoyl-1-methylpyrrole-2-acetate is heated at 250° for 10 minutes under nitrogen. It is then cooled and dissolved in ether; the resulting ether solution is filtered, washed with sodium hydroxide solution, and then washed with water. After the ether is evaporated in vacuo, the residue is triturated with boiling hexane. Concentration of the hexane solution to a small volume in vacuo yields a crystalline precipitate, which is recrystallized from methanol to give ethyl 4-bromo-5-(p-chlorobenzoyl)-1-methylpyrrole-2-acetate as a white solid; m.p. 118°-120° C.

EXAMPLE XVIII

4-Bromo-5-(p-chlorobenzoyl)-1-methylpyrrole-2-acetic acid

A suspension of 0.9 g. of ethyl 4-bromo-5-(p-chlorobenzoyl)-1-methylpyrrole-2-acetate in 5 ml of 0.5N sodium hydroxide solution containing a few drops of ethanol is heated under reflux for one hour. At the end of 1 hour it is cooled, diluted with water and filtered, and the filtrate washed with ether. The aqueous filtrate is then acidified with dilute hydrochloric acid and the resulting precipitated solid is collected and air dried. Recrystallization thereof from acetonitrile gives 4-bromo-5-(p-chlorobenzoyl)- 1-methylpyrrole-2-acetic acid as a pink solid; m.p. 190° C. (dec.)

Analysis: Calc'd for $C_{14}H_{11}BrClNO_3$: C, 47.15; H, 3.11%. Found: C, 47.38; H, 3.21%.

EXAMPLE XIX

Ethyl 1,2-dimethyl-5-(p-toluoyl)pyrrole-3-carboxylate

Thirty-seven grams of p-toluoyl chloride (0.243 mole) is added to a suspension of 32.4 g. (0.243 mole) of aluminum chloride in 80 ml of dichloroethane. The resulting solution is then added dropwise to a solution of 40.7 g. (0.243 mole) of ethyl 1,2-dimethylpyrrole-3-carboxylate in 80 ml of dichloroethane cooled in an ice bath. After the addition is complete, the resulting solution is stirred at room temperature for 20 minutes, is refluxed for 20 minutes, and is then poured into an ice-3N hydrochlorice acid mixture. The organic phase is separated and is washed twice with concentrated sodium chloride solution, after which it is dried over magnesium sulfate. Evaporation of the solvent yields a residue from which the desired product crystallized. Further product is obtained by chromatography of the mother liquor over acid-washed alumina in hexane using benzene as the eluant. Evaporation of the first compound-bearing fractions yields the desired product. Recrystallization of the combined yields of product from 95% ethanol and then methanol gives as pure product ethyl 1,2-dimethyl-5-(p-toluoyl)pyrrole-3-carboxylate; m.p. 98°-100° C.

EXAMPLE XX

Ethyl 4-bromo-1,2-dimethyl-5-(p-toluoyl)pyrrole-3-carboxylate

A solution of 27.4 ml (0.538 mole) of bromine in 150 ml of chloroform is added to a refluxing solution of 152.6 g. (0.538 mole) of ethyl 1,2-dimethyl-5-(p-toluoyl)pyrrole-3-carboxylate in 1500 ml of chloroform containing a few iodine crystals over a period of 45 min. The solution is heated under reflux for 10 min. and is then poured into ice water. The organic layer is separated and washed with sodium bicarbonate solution, sodium bisulfate solution, and brine. It is then dried over sodium sulfate and the solvent is evaporated in vacuo. After recrystallization of the product from methanol, it is extracted in a Soxhlet extractor with about one liter of diethyl ether and then crystallized from the cooled ether to yield ethyl 4-bromo-1,2-dimethyl-5-(p-toluoyl)-pyrrole-3-carboxylate; m.p. 122°-125° C.

EXAMPLE XXI

4-Bromo-1-methyl-5-(p-toluoyl)pyrrole-2-acetonitrile-3-carboxylate

A solution of 118.7 g. (0.326 mole) of ethyl 4-bromo-1,2-dimethyl-(5-p-toluoyl)-pyrrole-3-carboxylate in 750 ml of benzene is heated to reflux, and a mixture of 58 g (0.326 mole) of N-bromosuccinimide and 0.6 g. of dibenzoyl peroxide is added in portions over 30 minutes. The mixture is then heated under reflux for a further 45 minutes and is cooled. The precipitated succinimide is filtered off and the filtrate is evaporated to yield a residue containing ethyl 4-bromo-2-bromomethyl-1-methyl-5-(p-toluoyl)pyrrole-3carboxylate.

A solution of this residue in 400 ml of dimethyl sulfoxide is added to a suspension of 17.6 g. (0.358 mole) of sodium cyanide in 200 ml of dimethyl sulfoxide at a rate such that the temperature remains at about 45°. The mixture is then stirred for 20 minutes and is poured into water. The resulting mixture is extracted with ether and the ether extract is washed with water and brine and dried over magnesium sulfate. The solvent is evaporated in vacuo to give a yellow gum containing the desired product. Chromatography of this gum on silica with benzene and then 10% chloroform in benzene gives fractions containing the desired product. Evaporation of the solvent in vacuo followed by recrystallization of the residue from methanol and then from isopropanol gives ethyl 4-bromo-1--methyl-5-(p-toluoyl)pyrrole-2-acetonitrile-3-carboxylate as a white solid; m.p. 103°-105° C.

EXAMPLE XXII

4-Bromo-3-carboxyl-1-methyl-5-(p-tolouyl)pyrrole-2-acetic acid

To a refluxing mixture of 22.3 g. (0.057 mole) of 4-bromo-3-ethoxycarbonyl-1-methyl-5-(p-toluoyl)pyrrole-2-acetonitrile, 220 ml of ethanol, and 60 ml of water is added 57.2 ml of 1N sodium hydroxide solution over a period of 1 hour. The mixture is then heated under reflux for a further 1 hour, after which time 110 g of 50% sodium hydroxide solution is added. The mixture is heated under reflux for a further six hours. Pouring the resulting mixture into water and acidifying with dilute hydrochloric acid precipitates a solid, which solid is filtered off, washed with water and then partitioned between chloroform and aqueous sodium bicarbonate solution. The aqueous phase is separated, washed with diethyl ether and hexane, and acidified with dilute hydrochloric acid. The resulting precipitate is filtered off and recrystallized from acetone-water to yield 4-bromo-3-carboxyl-1-methyl-5-(p-toluoly)pyrrole-2-acetic acid; m.p. 230° C. (dec).

EXAMPLE XXIII

Ethyl 4-bromo-3-carboxyl-1-methyl-5-(p-toluoyl)pyrrole-2-acetate

A 10.5 g. sample of 4-bromo-3-carboxyl-1-methyl-5-(p-toluoyl)pyrrole-2-acetic acid is dissolved in 100 ml of 0.5% ethanolic hydrogen chloride by heating under reflux for 45 minutes. Part of the solvent is evaporated in vacuo, causing a precipitate to form. Collection and drying of this precipitate yields ethyl 4-bromo-3-carboxy-1-methyl-5-(p-toluoyl)pyrrole-2-acetate; m.p. 183°–185° C.

EXAMPLE XXIV

Ethyl 4-bromo-1-methyl-5-(p-toluoyl)pyrrole-2acetate

A solution of 8.0 g. (0.0195 mole) of ethyl 4-bromo-3-carboxy-1-methyl-5-(p-toluoly)pyrrole-2-acetate in 80 ml of quinoline with 0.8 g. of copper chromite added is heated under nitrogen at 200° for 3¼ copper. The mixture is then cooled and poured into ice-hydrochloric acid. The whole is extracted with diethyl ether, and the other solution is washed with hydrochloric acid, sodium bicarbonate solution, and brine and is dried over magnesium sulfate. Evaporation of the solvent in vacuo yields a black oil, which is chromatographed on silica (SILIC AR CC-4) with first hexane and then 50% benzene-hexane as eluants. After removal of front-running impurities with these eluants, benzene is used to elute the desired product. Evaporation of the benzene from the productbearing fraction and recrystallization of the residue from hexane yields ethyl 4-bromo-1-methyl-5-(p-toluoyl)pyrrole-2-acetate as a white solid; m.p. 85°–87° C.

EXAMPLE XXV

4-Bromo-1-methyl-5-(p-toluoyl)pyrrole-2-acetic acid

A suspension of 2.6 g. (0.0715 mole) of ethyl 4-bromo-1-methyl-5-(p-toluoyl)pyrrole-2-acetate in 14.4 ml of 0.5N sodium hydroxide solution is heated under reflux for 30 minutes. It is then poured into dilute hydrochloride acid and the precipitated solid is filtered and air dried. Recrystallization of this precipitate from ether by addition of cyclohexane and evaporation of the ether until crystallization occurs yields as a white solid 4-bromo-1-methyl-5-(p-toluoyl)pyrrole-2-acetic acid; m.p. 155°–157° C.

Analysis: Calc'd. for $C_{15}H_{14}BrNO_3$: C, 53.59; H, 4.70; N, 4.17%. Found: C, 53.63; H, 4.21; N, 4.09%.

EXAMPLE XXVI 1-(Pyrrole-2-ylmethylene)pyrrolidium bromide

To a solution of 81.0 g (1.00 mole) of hydrogen bromide in 1000 ml of absolute chloroform is added dropwise with cooling and stirring a solution of 80.0 g (1.12 mole) of pyrrolidine in 100 ml of absolute chloroform. Then 95.1 g (1.00 mole) of pyrrole-2-carboxaldehyde is added to the above pyrrolidine hydrobromide solution along with 1 pound of Linde Molecular sieve 5A. The reaction mixture is stirred at ambient temperature for 3 hours, then is filtered through filter aid, washing well with chloroform. The combined filtrate and washings are evaporated in vacuo and the residue is recrystallized twice from acetonitrile to give 1-(pyrrol-2-ylmethylene)pyrrolidinium bromide; m.p. 113°–116° C.

EXAMPLE XXVII 1-(4-Bromopyrrol-2-ylmethylene)pyrrolidinum bromide

To a solution of 91.0 g of 1-(pyrrol-2-ylmethylene)-pyrrolidmium bromide (0.397 mole) in 1300 ml of absolute chloroform is added dropwise with stirring and ice-cooling 63.4 g of bromine (0.397mole). A solid precipitates during addition. After the reaction mixture has been stirred at room temperature for 64 hours, the solvent is evaporated in vacuo and the residue is recrystallized from 3:1 chloroform-acetonitrile to give as an off-white solid 1-(4-bromopyrrole-2-ylmethylene)pyrrolidinium bromide; m.p. 226°–228° C.

EXAMPLE XXVIII

-b 4-Bromo-2-(1-pyrrolidinomethyl)pyrrole

A solution of 3.1 g (0.01 mole) of 1-(4-bromopyrrol-2-ylmethylene)pyrrolidinium bromide in 30 ml of absolute methanol is shaken with 0.15 g of 5% rhodium on carbon and 0.40 g of magnesium oxide (0.10 mole) in a hydrogen atomsphere under an initial pressure of 47 psi. After a half-hour the reaction mixture is filtered through filter aid, washing well with methanol. The combined filtrate and washings are evaporated in vacuo, the resulting residue is dissolved in 3N hydrochloric acid and the whole is washed with ether. The aqueous solution is treated with 10% aqueous sodium hydroxide solution until the pH reaches 12; it is then extracted several times with ether. (The combined extracts are washed with brine and are dried over potassium carbonate. Evaporation in vacuo gives an oily residue which crystallized; recrystallization twice from hexane gives a beige solid, 4-bromo-2-(1-pyrroledinymethyl)pyrrole; m.p. 96°–99° C.

EXAMPLE XXIX

4-Bromo-2-(1-pyrrolidinomethyl)pyrrole-borane complex

A suspension of 3.1 g of finely ground 1-(4-bromopyrrol-2-ylmethylene)pyrrolidinium bromide (0.01 mole) in 30 ml of dry tetrahydrofuran (THF) is stirred at room temperature under $N_2$ while 30 ml of 1M borane.- THF complex is added dropwise over 10 minutes with stirring, and the whole is stirred for a further 2¼ hours while being chilled in an ice bath. Then 10 ml of 1N NaOH is added dropwise and hydrogen is evolved. The reaction mixture is acidified and extracted with ether; the combined extracts are washed with brine and dried over potassium carbonate. Evaporation in vacuo gives as a light red viscous oil 4-bromo-2-(1-pyrrolidinemethyl)-pyrrole-borane complex. IR (neat): 3500, 3050, 2400, 2310 cm$^{-1}$.

EXAMPLE XXX

4-Bromo-2-(1-pyrrolidinomethyl)pyrrole 2.0 g of 4-bromo-2-(1-pyrrolidinomethyl)pyrrole-borane complex is dissolved in 10 ml of pyrrolidine, and the whole is stirred at ambient temperature for 72 hours, after which time the solvent is evaporated in vacuo. The residue is dissolved in 3N hydrochloric acid, and the resulting solution is successively washed with ether, treated with 10% aqueous sodium hydroxide solution until basic, and then extracted several times with ether. The combined extracts are washed with brine and are dried over potassium carbonate. Evaporation of the ether in vacuo and recrystallization of the resulting residue from hexane gives 4-bromo-2-(1-pyrrolidinomethyl)-pyrrole as a beige solid; m.p. 96°–99° C.

EXAMPLE XXXI

Following the procedure of Example VII, but substituting an equivalent amount of the 4-bromo-2-(1-pyrrolidinomethyl)pyrrole produced is Example XXVII or Example XXIX for the free base 4-chloro-2-(1-pyrrolidinomethyl)pyrrole used therein, there is prepared 4-bromopyrrol-2-acetonitrile.

EXAMPLE XXXII

4-Bromo-5-(p-chlorobenzoyl)pyrrole-2-acetonitrile

A solution of 0.90 g (0.005 mole) of 4-bromopyrrole-2-acetonitrile and 0.87 g of p-chlorobenzoyl chloride (0.0005 mole) in 10 ml of methylene chloride is chilled in a dry-ice acetone bath to −30° C and is stirred while treated with 0.58 mg of anhydrous stannic chloride (0.005 mole). An orange solid precipitates. The reaction mixture is allowed to warm slowly over 1 hour to 5° C and is poured and scraped into ice-water. The whole is extracted with chloroform and the combined organic layers are washed successively with aqueous N,N-dimethylamino-1,3-propanediamine, 3N hydrochloric acid, aqueous sodium bicarbonate solution, and brine, and are dried over sodium sulfate. The viscous oil which results from evaporation of the solvent is vacuo is chromatographed on silica gel (Mallinkrodt CC-7) packed with benzene and eluated with a benzene-ether gradient. The desired material is eluted with 15% ether in benzene and recrystallized from methanol to give 4-bromo-5-(p-chlorobenzoyl)pyrrole-2-acetonitrile as a beige solid; m.p. 185°–186° C.

EXAMPLE XXXIII

4-Bromo-5-(p-chlorobenzoyl)-1-methylpyrrole-2-acetontrile

A solution of sodium isoproxide is prepared by dissolving 0.25 g of sodium (0.011 mole) in 40 ml of isopropanol. To this solution 2.9 g (0.009 mole) of 4-bromo-5-p-chlorbenzoyl)-pyrrole-2-acetontrile and 10 ml of isopropanol are added all at once, followed by 1.05 mg (0.011 mole) of dimethylsulfate. The reaction mixture is refluxed for 45 minutes, after which it is poured into 150 ml of cold dilute hydrochloric acid. The yellow solid which precipitated is filtered off and washed well with water. Chromatographing this solids on 100 g of Baer's alumina packed with benzene and eluated with a enzene-ether gradient yields of desired product in the % ether-benzene fraction. This fraction is evaporated, nd the resulting solid is recrystallized twice from 1:1 thyl acetate-hexane to give 4-bromo-5-(p-chlorobenzoyl)-1-methylpyrrole-2-acetontrile as a white solid; m.p. 128.5°–130.0° C.

EXAMPLE XXXIV

4-Bromo-5-(p-chlorobenzoyl)-1-methylpyrrole-2-acetic acid

A solution of 0.05 g (1.1 m mole) of sodium hydroxide in 2 ml of water and 2 ml of ethanol is combined with 0.19 g (0.56 m mole) of 4bromo-5-(p-chlorobenzoyl)-1-methylpyrrole-2-acetnitrile, and the whole is stirred and refluxed for 4 hours. The resulting mixture is poured into 30 ml of cold 3N hydrochloric acid; the precipitate which forms is filtered off and washed well with water. Recrystallization of this precipitate from acetonitrile yields 4-bromo-5-(p-chlorobenzoyl)-1-methylpyrrole-2-acetic acid as a pink solid; m.p. 190° C. (dec.)

EXAMPLE XXXV

Following the procedure of Example XXXII, but substituting an equivalent amount of 4-chloropyrrole-2-acetonitrile and the appropriately substituted benzoyl chloride for the 4-bromopyrrole-2-acetontrile and p-chlorobenzoyl chloride, respectively, used therein, the following are prepared:

4-chloro-5-(p-bromobenzoyl)pyrrole-2-acetonitrile;
4-chloro-5-(p-methoxybenzoyl)pyrrole-2-acetonitrile;
4-chloro-5-(m-chlorobenzoyl)pyrrole-2-acetonitrile;
4-chloro-5-(3,4-dichlorobenzoyl)pyrrole-2-acetonitrile;
4-chloro-5-(2,4,6-trimethlbenzoyl)pyrrole-2-acetonitrile;
4-chloro-5-(p-trifluoromethylbenzoyl)pyrrole-2-acetonitrile;
4-chloro-5-(p-methylthiobenzoyl)pyrrole-2-acetonitrile.

EXAMPLE XXXVI

Following the procedure of Example IX, but substituting equivalent amounts of an appropriate compound made as in Example XXXV and an appropriate diloweralkyl sulfate for the 4-chloro-5-(p-chlorobenzoyl)pyrrole-2-acetontrile and dimethyl sulfate used therein, the following are prepared:

4-chloro-5-(p-bromobenzoyl)-1-methypyrrole-2-acetonitrile;
4-chloro-5-(p-methoxybenzoyl)-1-methylpyrrole-2-acetonitrile;
4-chloro-5-(m-chlorobenzoyl)-1-methlpyrrole-2-acetonitrile;
4-chloro-5-(3,4-dichlorobenzoyl)-1-methypyrrole-2-acetonitrile;
4chloro-5-(2,4,6-trimethylbenzoyl)-1-methylpyrrole-2-acetonitrile;
4-chloro-5-(2,4,6-trimethylbenzoyl-1-ethylpyrrole-2-acetonitrile;
4-chloro-5-(p-methoxybenzoyl)-1-ethylpyrrole-2-acetonitrile;
4-chloro-5-(m-chlorobenzoyl)-1-ethylpyrrole-2-acetonitrile;
4-chloro-5-(p-trifluoromethylbenzoyl)-1-methylpyrrole-2-acetonitrile;
4-chloro-5-(p-methylthiobenzoyl)-1-methylpyrrole-2-acetonitrile.

EXAMPLLE XXXVII

Following the procedure of Example XI, but substituting an equivalent amount of an appropriate compound made in Example XXXVI for the 4-chloro-5-(p-chlorobenzoyl)-1-methylpyrrole-2l -acetonitrile used therein, the following are prepared:

4-chloro-5-(p-bromobenzoyl)-1-methylpyrrole-2-acetic acid;
4-chloro-5-(p-methoxybenzoyl)-1-methylpyrrole-2-acetic acid;
4-chloro-5-(m-chorobenzoyl)-1-methypyrrole-2acetic acid;
4-chloro-5-(3,4-dichlorobenzoyl)-1-methylpyrrole-2a-cetic acid;
4-chloro-5-(2,46-trimethylbenzoyl)-1-methylpyrrole-2-acetic acid;
4-chloro-5-(2,4,6-trimethylbenzoyl)-1-ethylpyrrole-2-acetic acid;
4-chloro-5-(p-methoxybenzoyl)-1-ethylpyrrole-2-acetic acid;
4-chloro-5-(m-chlorobenzoyl)-1-ethylpyrrole-2acetic acid;
4-chloro-5-(p-trifluoromethylbenzoyl)-1-methylpyrrole-2-acetic acid;
4-chloro-5-(p-methylthiobenzoyl)-1-methylpyrrole-2-acetic acid.

EXAMPLE XXXVIII

Following the procedure of Example XXXII, but substituting an equivalent amount of the appropriately substituted benzoyl chloride for the p-chlorobenzoyl chloride used therein, the following are prepared:
4-bromo-5-(p-bromobenzoyl)pyrrole-2-acetonitrile;
4-bromo-5-(p-methoxybenzoyl)pyrrole-2-acetonitrile;
4-bromo-5-(m-chlorobenzoyl)pyrrole-2-acetonitrile;
4-bromo-5-(3,4-dichlorobenzoyl)pyrrole-2-acetonitrile;
4-bromo-5-(2,4,6-trimethylbenzoyl)pyrrole-2-acetonitrile;
4-bromo-5-(p-trifluoromethylbenzoyl)pyrrole-2-acetonitrile;
4-bromo-5-(p-methylthiobenzoyl)pyrrole-2-acetonitrile.

EXAMPLE XXXIX

Following the procedure of Example XXXVI, but substituting equivalent amounts of the corresponding 4-bromo compound made as in Example XXXVIII for the 4-chloro compounds used therein, the 4-bromo-1-loweralkyl compounds corresponding to those prepared therein are made.

Then following the procedure of Example XI, but substituting an equivalent amount of an appropriate bromo compound prepared above for the 4-chloro-5-(p-chlorobenzoyl)-1-methylpyrrole-2-acetonitrile used therein, the following are prepared:

4-bromo-5-(p-bromobenzoyl)-1-methylpyrrole-2-acetic acid;
4-bromo-5-(p-methoxybenzoyll)-1-methylpyrrole-2a-cetic acid;
4-bromo-5-(m-chlorobenzoyl)-1-methypyrrole-2-acetic acid;
4-bromo-5 -(3,4-dichlorobenzoyl)-1-methylpyrrole-2-acetic acid;
4-bromo-5-(2,4,6-trimethylbenzoyl)-1-methypyrrole-2-acetic acid;
4-bromo-5-(2,4,6-trimethylbenzoyl)-1-ethylpyrrole-2-acetic acid;
4-bromo-5-(p-methoxybenzoyl)-1-ethylpyrrole-2-acetic acid;
4-bromo-5-(m-chlorobenzoyl-1-ethylpyrrole-2-acetic acid;
4-bromo-5-(p-trifluoromethylbenzoyl)-1-methylpyrrole-2-acetic acid;
4-bromo-5-(p-methylthiobenzoyl)-1-methylpyrrole-2-acetic acid.

EXAMPLE XXXX

Following the procedure of Example X, but substituting the appropriate α-unsubstituted nitrile made in Examples XXXIII, XXXVI, and XXXIX and the appropriate loweralkyl iodide for the 4-chloro-5-(p-chlorobenzoyl)-1-methylpyrrole-2-acetonitrile and methyl iodide used therein, the following are prepared:

4-bromo-5-(p-chlorobenzoyl)-α-methyl-1-methylpyrrole-2-acetonitrile;
4-chloro-5-(p-bromobenzoyl)-α-ethyl-1-methylpyrrole-2-acetonitrile;
4-chloro-5-(p-methoxybenzoyl)-α-methyl-1-methylpyrrole-2-acetontrile;
4-chloro-5-(m-chlorobenzoyl)-α-methyl-1-methylpyrrole-2-acetonitrile;
4-chloro-5-(3,4-dichlorobenzoyl)-α-ethyl-1-methylpyrrole-2-acetonitrile;
4-chloro-5-(2,4,6-trimethylbenzoyl)-α-methyl-1-methylpyrrole-2-acetonitrile;
4-chloro-5-(2,4,6-trimethylbenzoyl)-α-methyl-1-ethylpyrrole-2-acetonitrile;
4-chloro-5-(p-methoxybenzoyl)-α-methyl-1-ethylpyrrole-2-acetonitrile
4-chloro-5-(m-chlorobenzoyl)-α-methyl-1-ethylpyrrole-2-acetonitrile;
4-chloro-5-(p-trifluoromethylbenzoyl)-α-methyl-1-methylpyrrole-2-acetonitrile;
4-chloro-5-(p-methythiobenzoyl)-α-methyl-1-methypyrrole-2-acetonitrile. 4-bromo-5-(p-bromobenzoyl)-α-ethyl-1-methylpyrrole-2-acetonitrile;
4-bromo-5-(p-methoxybenzoyl)-α-methyl-1-methylpyrrole-2-acetonitrile;
4-bromo-5-(m-chlorobenzoyl)-α-methyl-1-methylpyrrole-2-acetonitrile
4-bromo-5-(3,4-dichlorobenzoyl)-α-ethyl-1-methylpyrrole-2-acetonitrile;
4-bromo-5-(2,4,6-trimethylbenzoyl)-α-methyl-1-methylpyrrole-2-acetonitrile;
4-bromo-5-(2,4,6-trimethylbenzoyl)-α-methyl-1-ethylpyrrole-2-acetonitrile;
4-bromo-5-(p-methoxybenzoyl)-α-methyl-1-ethylpyrrole-2-acetonitrile;
4-bromo-5-(m-chlorobenzoyl)-α-methyl-1-ethylpyrrole-2-acetonitrile;
41 -bromo-5-(p-trifluoromethylbenzoyl)-α-methyl-1-methylpyrrole-2-acetonitrile;
4-bromo-5-(p-methylthiobenzoyl)-α-methyl-1-methypyrrole-2-acetonitrile.

EXAMPLE XXXXI

Following the procedure of Example XI, but substituting an equivalent amount of an appropriate compound made in Example X or XXXX for the 4-chloro-5-(p-chlorobenzoyl)-1methylpyrrole-2-acetonitrile used therein, the following are prepared:

4-chloro-5-(p-chlorobenzoyl)-α-methyl-1-methylpyrrole-2-acetic acid;
4-bromo-5-(p-chlorobenzoyl)-α-methyl-1-methylpyrrole-2-acetic acid;
4-chloro-5-(p-bromobenzoyl)-α-ethyl-1-methylpyrrole-2-acetic acid;
4-chloro-5-(pmethoxybenzoyl)-α-methyl-1-methylpyrrole-2-acetic acid;
4-chloro-5-(m-chlorobenzoyl)-α-methyl-1-methyl-pyrrole-2-acetic acid;
4-chloro-5-(3,4-dichlorobenzoyl)-α-ethyl-1-methyl-pirrole2-acetic acid;
4-chloro-5-(2,4,6-trimethylbenzoyl)-α-methyl-1-methylpyrrole-2-acetic acid;
4-chloro-5-(2,4,6-trimethylbenzoyl)-α-methyl-1-ethyl-pyrrole-2-acetic-acid;
4-chloro-5-(p-methoxybenzoyl)-α-methyl-1-ethylpyrrole-2-acetic acid;
4-chloro-5-(m-chlorobenzoly)-α-methyl-1-ethylpyrrole-2-acetic acid;
4-chloro-5-(p-trifluoromethylbenzoyl)-α-methyl-1-methylpyrrole-2-acetic acid;
4-chloro-5-(p-methylthiobenzoyl)-α-methyl-1-methyl-pyrrole-2-acetic acid;
4-bromo-5-(p-bromobenzoyl)-α-ethyl-1-methylpyrrole-2-acetic acid;
4-bromo-5-(p-methoxybenzoyl)-α-methyl-1-methylpyrrole-2-acetic acid;
4-bromo-5-(m-chlorobenzoyl)-α-methyl-1-methylpyrrole-2-acetic acid;
4-bromo-5-(3,4-dichlorobenzoyl)-α-ethyl-1-methylpyrrole-2-acetic acid;
4-bromo-5-(2,4,6-trimethylbenzoyl)-α-methyl-1-methylpyrrole-2-acetic acid;
4-bromo-5-(2,3,6-trimethylbenzoyl)-α-methyl-1-ethylpyrrole-2-acetic acid
4-bromo-5-(p-methoxybenzoyl)-α-methyl-1-ethylpyrrole-2-acetic acid;
4-bromo-5-(m-chlorobenzoyl)-α-methyl-1-ethylpyrrole-2-acetic acid;
4-bromo-5-(p-trifluoromethylbenzoyl)-α-methyl-1-methylpyrrole-2-acetic acid;
4-bromo-5-(p-methylthiobenzyoly)-α-methyl-1-methyl-pyrrole-2-acetic acid.

EXAMPLE XXXXII

Following the procedure of Example I, but substituting as equivalent amount of an appropriately substituted pyrrole-2-acetic acid for the 1-methyl-5-(p-toluoyl)pyrrole-2-acetic acid used therein, the following are prepared:

3-bromo-5-(p-bromobenzoyl)-1-methylpyrrole-2-acetic acid;
3-bromo-5-(p-methoxybenzoyl)-1-methylpyrrole-2-acetic acid;
3-bromo-5-(m-chlorobenzoyl)-1-methylpyrrole-2-acetic acid;
3-bromo-5-(3,4-dichlorobenzoyl)-1-methylpyrrole-2-acetic acid;
3-bromo-5-(2,4,6-trimethylbenzoyl)-1-methylpyrrole-2-acetic acid;
3-bromo-5-(2,4,6-trimethylbenzoyl)-1-ethylpyrrole-2-acetic acid;
3-bromo-5-(p-methoxybenzoyl)-1-ethylpyrrole-2-acetic acid;
3-bromo-5-(m-chlorobenzoyl)-1-ethylpyrrole-2-acetic acid;
3-bromo-5-(p-trifluoromethylbenzoyl)-1-methylpyrrole-2-acetic acid;
3-bromo-5-(p-methylthiobenzoyl)-1-methylpyrrole-2-acetic acid;
3-bromo-5-(p-bromobenzoyl)-α-ethyl-1-methylpyrrole-2-acetic acid;
3-bromo-5-(-p-methoxybenzoyl)-α-methyl-1-methyl-pyrrole-2-acetic acid;
3-bromo-5-(m-chlorobenzoyl)-α-methyl-1-methylpyrrole-2-acetic acid;
3-bromo-5-(3,4-dichlorobenzoyl)-α-ethyl-1-methylpyrrole-2-acetic acid;
3-bromo-5-(2,4,6-trimethylbenzoly)-α-methyl-1-methyl-pyrrole-2-acetic acid;
3-bromo-5-(2,4,6,-trimethylbenzoyl)-α-methyl-1-ethylpyrrole-2-acetic acid;
3bromo-5-(p-methoxybenzoyl)-α-methyl-1-ethylpyrrole-2-acetic acid;
3-bromo-5-(m-chlorobenzoyl)-α-methyl-1-ethylpyrrole-2-acetic acid;
3-bromo-5-(p-trifluoromethylbenzoyl)-α-methyl-1-methylpyrrole-2-acetic acid;
3-bromo-5-(p-methylthiobenzoyl)-α-methyl-1-methyl-pyrrole-2l -acetic acid;
3-bromo-5-(2,4-dimethythiobenzoyl)-α-methyl-1-methylpyrrole-2-acetic acid.

EXAMPLE XXXXIII

Following the procedure of Example II, but substituting an equivalent amount of an appropriately substituted pyrrole-2-acetate for the methyl 1-methyl-5-(p-toluoyl)pyrrole-2-acetic used therein, the following are prepared:

methyl 3-chloro-5-(p-bromobenzoyl)-1-methylpyrrole-2-acetate;
methyl 3-chloro-5-(p-methoxybenzoyl)-1-methylpyrrole-2-acetate;
ethyl 3-chloro-5-(m-chlorobenzoyl)-1-methylpyrrole-2-acetate;
ethyl 3-chloro-5-(3,4-dichlorobenzoyl)-1-methylpyrrole-2-acetate;
methyl 3-chloro-5-(2,4,6-trimethylbenzoyl)-1-methylpyrrole-2-acetate;
methyl 3-chloro-5-(2,4,6-trimethylbenzoyl)-1-ethylpyrrole-2-acetate;
methyl 3-chloro-5-(p-methoxybenzoyl-1-ethylpyrrole-2-acetate;
methyl 3-chloro-5-(m-chlorobenzoyl)-1-ethylpyrrole-2-acetate;
methyl 3-chloro-5-(p-trifluoromethylbenzoyl)-1-methylpyrrole-2-acetate;
methyl 3-chloro-5-(p-methylthiobenzoyl)-1-methylpyrrole-2-acetate;
methyl 3-chloro-5-(p-bromobenzoyl)-α-ethyl-1-methylpyrrole-2-acetate;
methyl 3-chloro-5-(p-methoxybenzoyl)-α-methyl-1-methylpyrrole-2-acetate;
3-chloro-5-(2,4,6-trimethylbenzoyl)-1-methylpyrrole-2-acetic acid;
3-chloro-5-(2,4,6-trimethylbenzoyl)-1-ethylpyrrole-2-acetic acid;
3-chloro-5-(p-methoxybenzoyl)-1-ethylpyrrole-2-acetic acid;
3-chloro-5-(m-chlorobenzoyl)-1-ethylpyrrole-2-acetic acid;

3-chloro-5-(p-trifluoromethylbenzoyl)-1-methylpyrrole-2-acetic acid;

3-chloro-5-(p-methylthiobenzoyl)-1-methylpyrrole-2-acetic acid;

3-chloro-5-(p-bromobenzoyl)-α-ethyl-1-methylpyrrole-2-acetic acid;

3-chloro-5-(p-methoxybenzoyl)-α-methyl-1-methylpyrrole-2-acetic acid;

3-chloro-5-(m-chlorobenzoyl)-α-methyl-1-methylpyrrole-2-acetic acid;

3-chloro-5-(3,4-dichlorobenzoyl)-α-ethyl-1-methylpyrrole-2-acetic acid;

3-chloro-5-(2,4,6-trimethylbenzoyl)-α-methyl-1-methylpyrrole-2-acetic acid;

3-chloro-5-(2,4,6-trimethylbenzoyl)-α-methyl-1-ethylpyrrole-2-acetic acid;

3-chloro-5-(p-methoxybenzoyl)-α-methyl-1-ethylpyrrole-2-acetic acid;

3-chloro-5-(m-chlorobenzoyl)-α-methyl-1-ethylpyrrole-2-acetic acid;

3-chloro-5-(p-trifluoromethylbenzoyl)-α-methyl-1-methylpyrrole-2-acetic acid;

3-chloro-5-(p-methylthiobenzoyl)-α-methyl-1-methylpyrrole-2-acetic acid.

ethyl 3-chloro-5-(m-chlorobenzoyl)-α-methyl-1-methylpyrrole-2-acetate;

ethyl 3-chloro-5-(3,4-dichlorobenzoyl)-α-ethyl-1-methylpyrrole-2-acetate;

methyl 3-chloro-5-(2,4,6-trimethylbenzoyl)-α-methyl-1-methylpyrrole-2-acetate;

methyl 3-chloro-5-(2,4,6-trimethylbenzoyl)-α-methyl-1-ethylpyrrole-2-acetate;

methyl 3-chloro-5-(p-methoxybenzoyl)-α-methyl-1-ethylpyrrole-2-acetate;

methyl 3-chloro-5-(m-chlorobenzoly)-α-methyl-1-ethylpyrrole-2-acetate;

methyl 3-chloro-5-(p-trifluoromethylbenzoyl)-α-methyl-1-methylpyrrole-2-acetate;

methyl 3-chloro-5-(p-methylthiobenzoyl)-α-methyl-1-methylpyrrole-2-acetate;

methyl 3-chloro-5-(2,4-ditrifluoromethyl benzoyl)-α-methyl-1-methylpyrrole-2-acetate.

EXAMPLE XXXIV

Following the procedure of Example III, but substituting the appropriate ester made in Example XXXXIII for the methyl 3-chloro-1-methyl-5-(p-toluoyl)pyrrole-2-acetate used therein, the following are prepared:

3-chloro-5-(p-bromobenzoyl)-1-methylpyrrole-2-acetic acid;

3-chloro-5-(p-methoxybenzoyl)-1-methylpyrrole-2-acetic acid;

3-chloro-5-(m-chlorobenzoyl)-1-methylpyrrole-2-acetic acid;

3-chloro-5-(3,4-dichlorobenzoyl)-1-methylpyrrole-2-acetic acid;

3-chloro-5-(2,4-ditrifluoromethylbenzoyl)-α-methyl-1-methylpyrrole-2-acetic acid.

EXAMPLE XLV

4-Chloro-1-methyl-5-(p-methylsulfinylbenzoyl)-pyrrole-2-acetonitrile: p To a suspension of 0.50 g of 4-chloro-1-methyl-5-(p-thiomethylbenzoyl)-pyrrole-2-acetonitrile in 10 ml of glacial acetic acid is added 0.16 ml of 30% aqueous hydrogen peroxide. The resulting mixture is stirred at room temperature for 18 hours, after which time it is poured into water and extracted with chloroform. The extract is washed with brine and dried over magnesium sulfate. Evaporation of the chloroform from the dried extract yields a yellow oil which crystallizes when scratched. Recrystallization of the product from chloroform yields 4-chloro-1-methyl-5-(p-methylsulfinylbenzoyl)-pyrrole-2-acetonitrile; m.p. 139°–141° C.

EXAMPLE XLVI

4-Chloro-1-methyl-5-(p-methylsulfinylbenzoyl)-pyrrole-2-acetic acid

A suspension of 0.50 g of 4-chloro-1-methyl-5-(p-methylsulfinylbenzoyl)-pyrrole-2-acetonitrile from Example XLV is stirred and refluxed in a solution of 0.13 g sodium hydroxide in 2 ml H₂O and 2 ml 95% ethanol for 2 hours. The whole is then poured into water and the resulting aqueous solution is washed with chloroform. The washed aqueous solution is then acidified to pH 1 with 3N HCl. The solid which precipitates is collected by filtration and is recrystallized from 10:1 chloroform: water to give 4-chloro-1-methyl-5-(p-methylsulfinylbenzoyl)-pyrrole-2-acetic acid as a yellow solid; m.p. 222°–223° C.

1. A halo-substituted 1-loweralkyl-5-aroylpyrrole-2-acetic acid compound of formula:

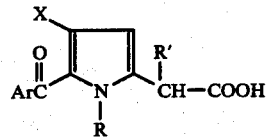

wherein X is a member selected from the group consisting of chloro and bromo, R is loweralkyl, R' is a member selected from the group consisting of hydrogen and loweralkyl, and Ar is a member selected from the group consisting of phenyl and phenyl substituted with from one to three members each selected from the group consisting of halo, loweralkyl, loweralkoxy, trifluoromethyl, methylthio, and methylsulfinyl provided that no more than two are selected from the group consisting of trifluoromethyl, methylthio, and methylsulfinyl.

2. A halo-substituted 1-loweralkyl-5-aroylpyrrole-2-acetic acid compound of formula:

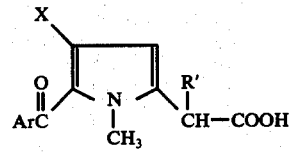

wherein Ar is a member selected from the group consisting of phenyl and phenyl substituted in the para position by a member selected from the group consisting of halo, loweralkyl and loweralkoxy, X is a member selected from the group consisting of chloro and bromo, and R' is a member selected from the group consisting of hydrogen and loweralkyl.

3. 4-Bromo-5-(p-toluoyl)-1-methylpyrrole-2-acetic acid.

4. 4-Chloro-5-(p-chlorobenzoyl-1-methylpyrrole-2-acetic acid.

5. 4-Bromo-5-(p-chlorobenzoyl)-1-methylpyrrole-2-acetic acid.

6. A halo-substituted 5-aroylpyrrole-2-acetonitrile compound of formula:

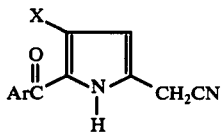

wherein X is a member selected from the group consisting of chloro and bromo and Ar is a member selected from the group consisting of phenyl and phenyl substituted with from one to three members each selected from the group consisting of halo, loweralkyl, loweralkoxy, trifluoromethyl, methylthio, and methylsulfinyl provided that no more than two are selected from the group consisting of trifluoromethyl, methylthio, and methylsulfinyl.

7. 4-bromo-5-(p-toluoyl)pyrrole-2-acetonitrile.
8. 4-chloro-5-(p-chlorobenzoyl)pyrrole-2-acetonitrile.
9. 4-bromo-5-(p-chlorobenzoyl)pyrrole-2-acetonitrile.
10. A bromo-substituted 1-loweralkyl-5-aroylpyrrole-2-acetate compound of formula:

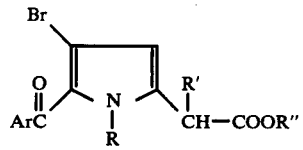

wherein R is loweralkyl, R' is a member selected from the group consisting of hydrogen and loweralkyl, R" is loweralkyl, and Ar is a member selected from the group consisting of phenyl and phenyl substituted with from one to three members each selected from the group consisting of halo, loweralkyl, loweralkoxy, trifluoromethyl, methylthio, and methylsulfinyl provided that no more than two are selected from the group consisting of trifluoromethyl, methylthio, and methylsulfinyl.

11. Ethyl 4-bromo-5-(p-chorobenzoyl)-1-methyl-pyrrole-2-acetate 12. 4-Chloro-1-methyl-5-(p-methylsulfinylbenzoyl)-pyrrole-2-acetic acid.

* * * * *

UNITED STATES PATENT AND TRADEMARK OFFICE
CERTIFICATE OF CORRECTION

PATENT NO. : 4,048,191

DATED : September 13, 1977

INVENTOR(S) : John Robert Carson

Page 1 of 3

It is certified that error appears in the above-identified patent and that said Letters Patent are hereby corrected as shown below:

At Column 4, Line 40, "[N-BH$_3$ structure]" should be -- [N-BH$_3$ structure with dot] --.

At Column 6, Formula XIV, " $\xrightarrow{R''OH}$ " should be -- $\xrightarrow[HCl]{R''OH}$ --.

At Column 7, Line 5, "about 40,20C" should be -- about 40°C. --

At Column 7, Line 16, "bromide" should be -- bromine --.

At Column 7, Line 55, "ArCOI" should be -- ArCOCl --.

At Column 8, Formula XIX, "CH$_2$BR" should be -- CH$_2$Br --.

At Column 11, Line 27, "61.83" should be -- 61.63 --.

At Column 11, Line 33, "IN" should be -- 1N --.

At Column 11, Line 52, "recrystalllized" should be -- recrystallized --.

At Column 12, Line 6, "1 1" should be -- 1:1 --.

At Column 14, Line 53, "methycyclohexane" should be -- methylcyclohexane --.

At Column 15, Line 62, "hydrochlorice" should be -- hydrochloric --.

At Column 16, Line 61, "carboxyl" should be -- carboxy --.

At Column 17, Line 11, "carboxyl" should be -- carboxy --.

At Column 17, Line 16, "carboxyl" should be -- carboxy --.

At Column 17, Line 18, "carboxyl" should be -- carboxy --.

At Column 17, Line 32, "3 1/2 copper" should be -- 3 1/2 hours --.

UNITED STATES PATENT AND TRADEMARK OFFICE
CERTIFICATE OF CORRECTION

PATENT NO. : 4,048,191
DATED : September 13, 1977
INVENTOR(S) : John Robert Carson It is certified that error appears in the above-identified patent and that said Letters Patent are hereby corrected as shown below:

At Column 17, Line 35, "other" should be -- ether --.
At Column 17, Line 55, "hydrochloride" should be -- hydrochloric --.
At Column 17, Line 64, "pyrrolidium" should be -- pyrrolidinium --.
At Column 18, Line 14, "pyrrolidinum" should be -- pyrrolidinium --.
At Column 18, Line 18, "pyrrolidmium" should be -- pyrrolidinium --.
At Column 18, Line 25, "bromopyrrole" should be -- bromopyrrol--
At Column 18, Line 29, "-b" should be deleted.
At Column 18, Line 48, "pyrroledinymethyl" should be -- pyrrolidinomethyl --.
At Column 18, Line 67, "pyrrolidinemethyl" should be -- pyrrolidinomethyl --.
At Column 19, Line 21, "is" should be -- in --.
At Column 19, Line 24, "bromopyrrol-" should be -- bromopyrrole-
At Column 19, Line 42, "is vacuo" should be -- in vacuo --.
At Column 19, Line 57, "acetontrile" should be -- acetonitrile--
At Column 19, Line 58, "1.05 mg" should be -- 1.05 ml --.
At Column 20, Line 1, "acetontrile" should be -- acetonitrile--.
At Column 20, Line 11, "acetnitrile" should be -- acetonitrile--
At Column 20, Line 23, "acetontrile" should be -- acetonitrile--
At Column 20, Line 44, "acetontrile" should be -- acetonitrile--

UNITED STATES PATENT AND TRADEMARK OFFICE
CERTIFICATE OF CORRECTION

PATENT NO. : 4,048,191

Page 3 of 3

DATED : September 13, 1977

INVENTOR(S) : John Robert Carson

It is certified that error appears in the above-identified patent and that said Letters Patent are hereby corrected as shown below:

At Column 21, Line 6, "methylpyrrole-21" should be -- methylpyrrole-2 --.
At Column 21, Line 13, "chorobenzoyl" should be -- chlorobenzoyl --.
At Column 22, Line 58, "41-bromo" should be -- 4-bromo --.
At Column 22, Line 61, "methypyrrole" should be -- methylpyrrole --.
At Column 23, Line 12, "pirrole 2" should be -- pyrrole-2 --.
At Column 23, Line 20, "chlorobenzoly" should be -- chlorobenzoyl --.
At Column 23, Line 44, "methylthiobenzyoly" should be -- methylthiobenzoyl --.
At Column 24, Line 15, "trimethylbenzoly" should be -- trimethylbenzoyl --.
At Column 22, Line 66, "XXXX" should be -- XL --.
At Column 25, Line 50, "XXXIV" should be -- XLIV --.
At Column 25, Line 53, "XXXXIII" should be -- XLIII --.
Examples 40-44, "XXXX" should be -- XL --.
At Column 26, Line 4, "p To" should be -- To --.
At Column 26, Line 31, "chloroform: water" should be -- chloroform:water --.
In the Claims, before the Claims, insert -- WHAT IS CLAIMED IS--

Signed and Sealed this

Ninth Day of January 1979

[SEAL]

Attest:

RUTH C. MASON
Attesting Officer

DONALD W. BANNER
Commissioner of Patents and Trademarks